United States Patent
Turos et al.

(10) Patent No.: US 8,414,926 B1
(45) Date of Patent: Apr. 9, 2013

(54) NANOPARTICLES WITH COVALENTLY BOUND SURFACTANT FOR DRUG DELIVERY

(75) Inventors: Edward Turos, Wesley Chapel, FL (US); Kerriann Robyn Greenhalgh, Tampa, FL (US); Julio Cesar Garay, Tampa, FL (US)

(73) Assignee: University of South Florida, Tampa, FL (US)

(*) Notice: Subject to any disclaimer, the term of this patent is extended or adjusted under 35 U.S.C. 154(b) by 1576 days.

(21) Appl. No.: 11/854,380

(22) Filed: Sep. 12, 2007

Related U.S. Application Data

(60) Provisional application No. 60/843,980, filed on Sep. 12, 2006.

(51) Int. Cl.
*A61K 9/10* (2006.01)
*A61K 9/107* (2006.01)

(52) U.S. Cl. ...................................................... 424/489

(58) Field of Classification Search .................. None
See application file for complete search history.

(56) References Cited

U.S. PATENT DOCUMENTS

| | | | |
|---|---|---|---|
| 4,826,689 | A | 5/1989 | Violanto |
| 5,145,684 | A | 9/1992 | Liversidge et al. |
| 5,162,475 | A | 11/1992 | Tang et al. |
| 5,510,118 | A | 4/1996 | Bosch et al. |
| 5,534,270 | A | 7/1996 | De Castro |
| 6,391,537 | B2 | 5/2002 | Lelental et al. |
| 7,030,175 | B2 | 4/2006 | Vincent et al. |
| 2002/0042394 | A1* | 4/2002 | Hogenkamp et al. ........... 514/53 |
| 2004/0063831 | A1* | 4/2004 | Sheppard et al. ............. 524/236 |
| 2006/0280798 | A1 | 12/2006 | Ensoli |
| 2007/0190160 | A1* | 8/2007 | Turos et al. .................... 424/490 |

FOREIGN PATENT DOCUMENTS

| | | |
|---|---|---|
| WO | WO 97/14443 | 4/1997 |
| WO | WO 99/59548 | 11/1999 |
| WO | WO 03/087180 | 10/2003 |
| WO | WO 2005/020933 | 3/2005 |
| WO | WO 2006/014138 | 2/2006 |

OTHER PUBLICATIONS

Schoonbrood, H. et al., "Reactive Surfactants in Heterophase Polymerization. 9. Optimum Surfmer Behavior in Emulsion Polymerization" *Macromolecules*, 1997, pp. 6034-6041, vol. 30.

Unzue, M. et al., "Reactive Surfactants in Heterophase Polymerization. VI. Synthesis and Screening of Polymerizable Surfactants (Surfmers) with Varying Reactivity in High Solids Styrene-Butyl Acrylate—Acrylic Acid Emulsion Polymerization" *J. Appl. Polym, Sci.*, 1997, pp. 1803-1820, vol. 66.

Giacomo Fontana et al. 'Amoxicillin-loaded polyethylcyanoacrylate nanoparticles: Influence of PEG coating on the particle size, drug release rate and phagocytic uptake.' Biomaterials. vol. 22, pp. 2857-2865, 2001.

Giacomo Fontana et al. 'Preparation, characterization and in vitro antimicrobial activity of ampicillin-loaded polyethylcyanoacrylate nanoparticles.' Biomaterials. vol. 19, pp. 1009-1017, 1998.

* cited by examiner

*Primary Examiner* — Anand Desai
*Assistant Examiner* — Melissa Mercier
(74) *Attorney, Agent, or Firm* — Saliwanchik, Lloyd & Eisenschenk

(57) ABSTRACT

The present invention concerns nanoparticles, compositions comprising the nanoparticles, methods for their production, and methods of using the nanoparticles for the delivery of biologically active agents (e.g., antibiotics or other drugs) to human or non-human subjects. In one embodiment, the nanoparticle is a "surfactant-free" nanoparticle in which the surfactant moiety is covalently attached to the backbone of the polymer.

17 Claims, 11 Drawing Sheets

SEM Image

TEM Image

DLS Image

NANOPARTICLES WITH COVALENTLY BOUND SURFACTANT FOR DRUG DELIVERY

CROSS-REFERENCE TO RELATED APPLICATION

The present application claims the benefit of U.S. Provisional Application Ser. No. 60/843,980, filed Sep. 12, 2006, which is hereby incorporated by reference herein in its entirety, including any figures, tables, nucleic acid sequences, amino acid sequences, and drawings.

GOVERNMENT SUPPORT

The subject matter of this application has been supported by research grants from the National Institutes of Health under grant number RO1 AI51351 and the National Science Foundation under grant number DGE 0221681. Accordingly, the government has certain rights in this invention.

BACKGROUND OF THE INVENTION

The term "controlled release" refers to the release of an agent such as a drug from a composition or dosage form in which the agent is released according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic or diagnostic response as compared to conventional rapid release dosage forms. Such longer periods of response provide for many inherent benefits that are not achieved with the corresponding short acting, immediate release preparations. For example, in the treatment of chronic pain, controlled release formulations are often highly preferred over conventional short-acting formulations.

Controlled release pharmaceutical compositions and dosage forms are designed to improve the delivery profile of agents, such as drugs, medicaments, active agents, diagnostic agents, or any substance to be internally administered to an animal, including humans. A controlled release composition is typically used to improve the effects of administered substances by optimizing the kinetics of delivery, thereby increasing bioavailability, convenience, and patient compliance, as well as minimizing side effects associated with inappropriate immediate release rates such as a high initial release rate and, if undesired, uneven blood or tissue levels.

The term "bioavailability" is used to describe the degree to which a drug becomes available at the site(s) of action after administration. The degree and timing in which an agent such as a drug becomes available to the target site(s) after administration is determined by many factors, including the dosage form and various properties such as dissolution rate of the drug. It is well known that some drug compositions suffer from poor bioavailability because of poor solubility of the active ingredient itself.

Numerous methods have been developed for enhancing the bioavailability of poorly soluble drugs. Particle size reduction, such as nanoparticulate forms of the agent, is one such method since the dissolution rate of a compound is related to the particle size. A nanoparticle is a sub-micron particle, the size of which is measured in nanometers (having at least one dimension of less than 100 nanometers). Nanoparticulate compositions comprise poorly water-soluble drug or agent particles having an extremely small particle size, i.e., less than one micron. With a decrease in particle size, and a consequent increase in ratio of surface area/mass, a composition tends to be rapidly dissolved and absorbed following administration. For certain formulations, this characteristic can be highly desirable, as described, for example, in U.S. Pat. Nos. 5,145,684; 5,510,118; 5,534,270; and 4,826,689; which are specifically incorporated by reference. However, rapid dissolution is contrary to the goal of controlled release.

Emulsion polymerization is a popular and well-known polymerization method for preparing uniform polymeric microspheres composed of relatively hydrophobic monomers (Esumi, K., *Polymer Interfaces and Emulsions*, Marcel Dekker, New York, 1999). Usually, this polymerization system consists of a hydrophobic monomer, water, and emulsifier such as a sodium salt of long-chain aliphatic acids and a water-soluble initiator. Nevertheless, factors such as nucleation and stability of the particles, and emulsification of the monomer droplets, not only during the polymerization process but also during the shelf life of the preparations, could be affected because of the presence of the surfactant (Unzue, M. et al., *J. Appl. Polym. Sci.*, 1997, 66:1803). Any unbound surfactant can migrate, forming aggregates that increase the sensitivity of the product and cause plasticization by water (Schoonbrood, H. and Asua, J. M., *Macramolecules*, 1997, 30:6034) and other undesirable effects on the stability and effectiveness of the products. A potential solution involves using reactive surfactants to assure that all of the surfactant is bound covalently to the polymer material and not present in unbound form in the aqueous media. It has been reported that migration of unbound surfactant can modify adhesion, water sensitivity and the optical properties, affecting the stability of the emulsion, especially when it is used as a drug delivery system.

BRIEF SUMMARY OF THE INVENTION

The present invention concerns nanoparticles, compositions comprising the nanoparticles, methods for their production, and methods of using the nanoparticles for the delivery of biologically active agents (e.g., antibiotics or other drugs) to human or non-human subjects. In one embodiment, the nanoparticle is a "surfactant-free" nanoparticle in which the surfactant moiety is covalently attached to the backbone of the polymer.

Recent research in the inventors' laboratory has involved the development of nanoparticles, such as polyacrylate and polyacrylamide nanoparticles, prepared in water emulsions. These nanoparticle emulsions can be used to deliver various biologically active agents such as antibiotics or other drugs. For example, nanoparticle emulsions of the invention can be used for treatment of life-threatening bacterial infections such as those caused by methicillin-resistant *Staphylococcus aureus* and *Bacillus anthracis*.

One aspect of the invention concerns a nanoparticle comprising an emulsified polymer having a biologically active agent covalently attached to the polymer backbone. In one embodiment the polymer is polyacrylate or polyacrylamide. In another embodiment, the polymer is a co-polymer comprising two or more types of monomer. In another embodiment, the biologically active agent is a water-insoluble drug. In another embodiment, the biologically active agent is an antibiotic, such as an N-thiolated β-lactam antibiotic. In another embodiment, the biologically active agent is covalently attached to the polymer backbone by an acryloyl amino acid.

The inventors have determined that some or all of the undesirable effects on stability and effectiveness of drug delivery products can be avoided by binding the surfactant moiety covalently to the polymer material. An advantage of this is that incorporation of the surfactant moiety into the polymer chain does not necessarily affect the molecular weight or the rate of polymerization. Once the surfactant is incorporated by copolymerization, the modified surfactant cannot desorb from the polymer material under most conditions, unless the polymer chain itself migrates through the polymer material. These nanoparticles are thus effectively "surfactant free". Accordingly, in each of the aforementioned embodiments, the nanoparticle further comprises a surfactant covalently attached to the polymer backbone.

Another aspect of the invention concerns a pharmaceutical composition comprising nanoparticles of the invention and a pharmaceutically acceptable carrier.

Another aspect of the invention concerns a method for producing a nanoparticle comprising an emulsified polymer having a biologically active agent covalently attached to the polymer backbone, the method comprising mixing the biologically active agent and a solution comprising monomers that has been pre-emulsified with a surfactant; adding an initiator to the solution; and allowing the monomers to polymerize.

Another aspect of the invention concerns a method for producing a nanoparticle, comprising co-polymerizing a monomer, a biologically active agent, and a surfactant, resulting in a nanoparticle comprising a polymer, the biologically active agent, and the surfactant, in which the biologically active agent and the surfactant are covalently attached to the polymer backbone.

BRIEF DESCRIPTION OF THE DRAWINGS

FIG. 7A is a graph showing a spectrophotometric calibration curve for anthracene-acrylate monomer at 364 nanometers. FIG. 7B is a graph showing a fluorescence calibration curve for anthracene-acrylate monomer.

FIGS. 11-1 and 11-2 show a representation of an N-thiolated β-lactam nanoparticle (FIG. 11-1) and a transmission electron micrograph showing the nanoparticle interacting with the cell membrane of an *S. aureus* microbe.

DETAILED DESCRIPTION OF THE INVENTION

Figure 1:
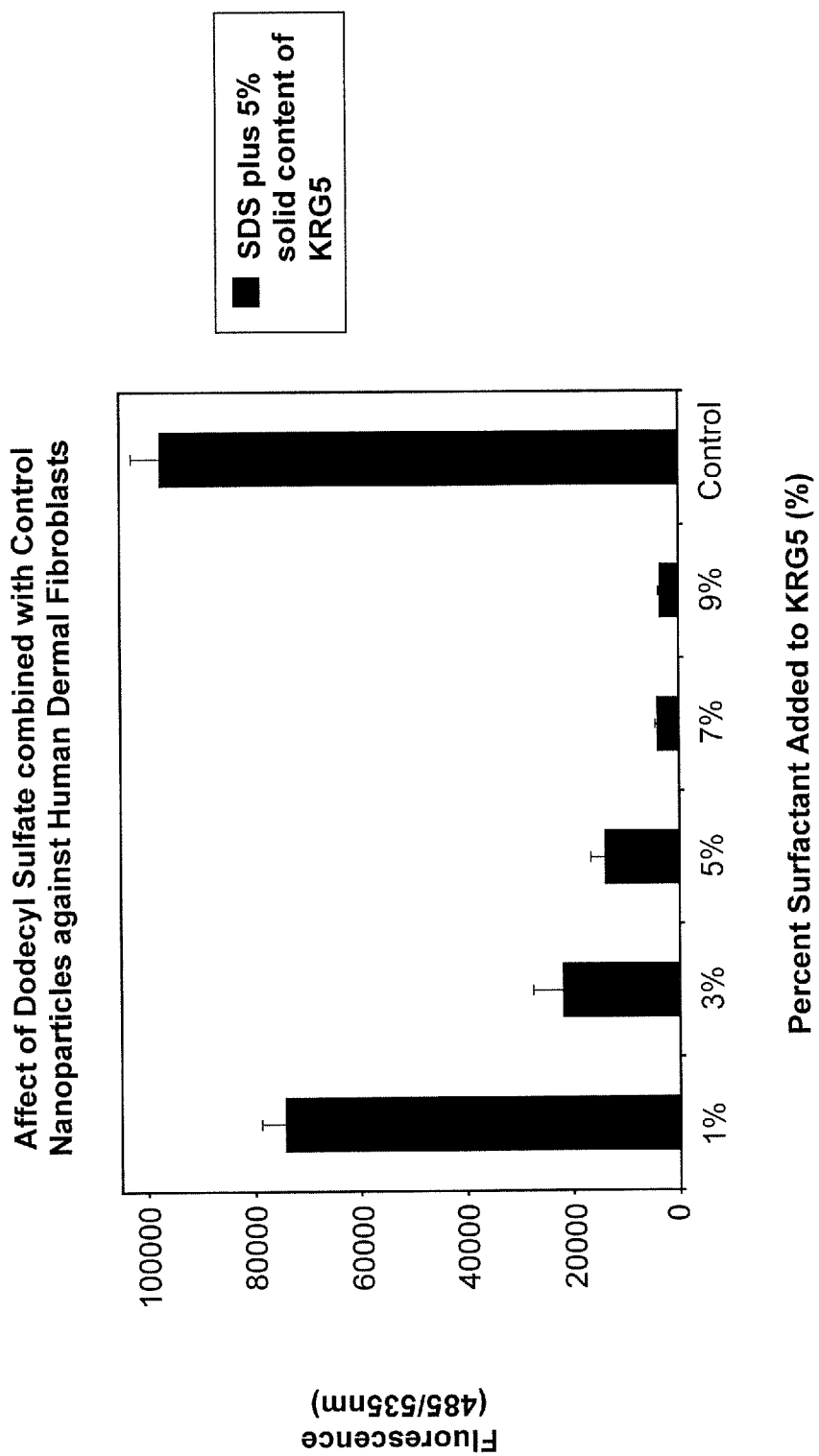
FIG. 1 is a graph showing the effect of dodecyl sulfate combined with control nanoparticles against human dermal fibroblasts.

The present invention concerns polymer nanoparticles, such as polyacrylate and polyacrylamide nanoparticles, prepared in water emulsions. These nanoparticle emulsions can be used for delivery of biologically active agents, such as drugs, to human or animal subjects (e.g., for treatment and/or prophylaxis). For example, in embodiments in which the biologically active agent is an N-thiolated β-lactam, treatment of life-threatening bacterial infections such as those caused by methicillin-resistant *Staphylococcus aureus* and *Bacillus anthracis* can be carried out. One of the disadvantages observed with such polymeric antibiotics is that the surfactant used for the polymerizations can leach away from the nanoparticle in high enough concentrations and cause cytotoxic effects in human fibroblast cells. To circumvent this, we are investigating the development of new types of nanoparticles in which the surfactant molecule is covalently attached to the backbone of the polymer. The synthesis and characterization of these "surfactant-free" nanoparticle systems, and their application to drug delivery, will be discussed.

As indicated above, an advantage of binding the surfactant moiety covalently to the polymer chain is that the incorporation does not necessarily affect the molecular weight or the rate of polymerization. Once the surfactant is incorporated by copolymerization, the modified surfactant cannot desorb from the polymer material under most conditions, unless the polymer chain itself migrates through the polymer material. These embodiments of the nanoparticles of the invention are thus effectively "surfactant free". However, an embodiment of the invention is a composition comprising nanoparticles having a surfactant moiety covalently bound to the polymer backbone; and one or more unbound surfactants.

Any surfactant can be used in the nanoparticles and production methods of the invention, including, for example, one or more anionic, cationic, non-ionic (neutral), and/or Zwitterionic surfactants. Examples of anionic surfactants include, but are not limited to, sodium dodecyl sulfate (SDS), ammonium lauryl sulfate, other alkyl sulfate salts, sodium laureth sulfate (also known as sodium lauryl ether sulfate: SLES), or Alkyl benzene sulfonate. Examples of cationic surfactant include, but are not limited to, alkyltrimethylammonium salts, cetylpyridinium chloride (CPC), polyethoxylated tallow amine (POEA), benzalkonium chloride (BAC), and benzethonium chloride (BZT). Examples of Zwitterionic surfactant include, but are not limited to, dodecyl betaine, dodecyl dimethylamine oxide, cocamidopropyl betaine, and coco ampho glycinate. Examples of nonionic surfactant include, but are not limited to, alkyl poly(ethylene oxide), or alkyl polyglucosides (octyl glucoside and decyl maltoside).

Any monomer can be used in the nanoparticles and production methods of the invention. Preferably, the monomer utilized is an acrylic monomer, a vinyl monomer, or a modified resin of either. Monomers utilized by the subject invention include, but are not limited to, acrylonitrile, acrylic acid, maleic acid, methyl acrylate, ethyl acrylate, butyl acrylate, butyl methacrylate, 2-ethylhexyl acrylate, methoxyethyl acrylate, dimethylamino acrylate, methacrylic acid, isobutyl methacrylate, 2-ethyl hexyl methacrylate, lauryl methacrylate, stearic methacrylate, dimethyl amino methacrylate, allyl methacrylate, 2-hydroxyethyl acrylate, 2-hydroxy propyl acrylate, 2-hydroxy ethyl methacrylate, modified acrylamide, modified methacrylamide glycidyl acrylate, styrene, vinyl acetate, vinyl toluene, and synthetically modified acrylics. Preferably, the monomer is ethyl acrylate.

The free-radicals utilized in the production methods of the subject invention include, but are not limited to, peroxides; persulphates; alkyl hydroperoxides; sodium, ammonium, and potassium salts of persulphate; thiosulphates; metabisulphites; and hydrosulphides. The initiator must be water soluble, and the free radicals may be generated thermally or by use of an oxidation-reduction (or redox) couple. The major initiators used in emulsion polymerization are persulphates. Even though initiating efficiency and half life of persulphates vary, ammonium persulphate is preferred in practice because of its better solubility. Hydroperoxides are often used particularly as a post reaction initiator to kill the unreacted monomers after emulsion polymerization.

The rate of free radical generation increases with temperature, and it is normal to employ reaction temperatures of 60-90° C. when using thermal generation techniques. However, when redox couples (thiosulphates, metabissulphites, and hydrosulphides) are employed, the rate of free radical generation is increased to that provided by thermal generation at the same temperature. Therefore, when using redox couples, reaction temperatures can be made as low as 30° C., or even room temperature. The free radicals can be added as an aqueous solution repeatedly until a milky solution is formed.

The aqueous media utilized in the pre-emulsifying and initiating steps include de-ionized water or nano-pure water. As known to those skilled in the art, a buffer solution may be necessary depending on the surfactant and particle stabilization.

The type of reaction vessel or vessels utilized for producing the nanoparticles of the invention, and the sizes of the vessels, are not critical. Any vessel or substrate capable of holding or supporting the reactants so as to allow the reaction to take place can be used. It should be understood that, unless expressly indicated to the contrary, the terms "adding", "contacting", "mixing", "reacting", "combining" and grammatical variations thereof, are used interchangeable to refer to the mixture of reactants of the process of the present invention (e.g., monomer, biologically active agent, polymerization initiator, surfactant, and so forth), and the reciprocal mixture of those reactants, one with the other (i.e., vice-versa).

Nanoparticles of the invention can include targeting moieties. As used herein, the terms "targeting moiety" and "targeting agent" are used interchangeably and are intended to mean any agent, such as a functional group, that serves to target or direct the nanoparticle to a particular location or association (e.g., a specific binding event). Thus, for example, a targeting moiety may be used to target a molecule to a specific target protein or enzyme, or to a particular cellular location, or to a particular cell type, to selectively enhance accumulation of the nanoparticle. Suitable targeting moieties include, but are not limited to, polypeptides, nucleic acids, carbohydrates, lipids, hormones including proteinaceous and steroid hormones, growth factors, receptor ligands, antigens and antibodies, and the like. For example, as is more fully outlined below, the nanoparticles of the invention may include a targeting moiety to target the nanoparticles (including biologically active agents associated with the nanoparticles) to a specific cell type such as tumor cells, such as a transferrin moiety, since many tumor cells have significant transferrin receptors on their surfaces. Similarly, a targeting moiety may include components useful in targeting the nanoparticles to a particular subcellular location. As will be appreciated by those in the art, the localization of proteins within a cell is a simple method for increasing effective concentration. For example, shuttling a drug into the nucleus confines them to a smaller space thereby increasing concentration. The physiological target may simply be localized to a specific compartment, and the agent must be localized appropriately. More than one targeting moiety can be conjugated or otherwise associated with each nanoparticle, and the target molecule for each targeting moiety can be the same or different.

Thus, suitable targeting sequences include, but are not limited to, binding sequences capable of causing binding of the moiety to a predetermined molecule or class of molecules, while retaining bioactivity of the expression product, (for example by using enzyme inhibitor or substrate sequences to target a class of relevant enzymes); sequences signaling selective degradation, of itself or co-bound proteins; and signal sequences capable of constitutively localizing the candidate expression products to a predetermined cellular locale, including (a) subcellular locations such as the Golgi, endoplasmic reticulum, nucleus, nucleoli, nuclear membrane, mitochondria, chloroplast, secretory vesicles, lysosome, and cellular membrane; and (b) extracellular locations via a secretory signal. Particularly preferred is localization to either subcellular location.

The targeting moiety can function to target or direct the nanoparticle to a particular location, cell type, diseased tissue, or association. In general, the targeting moiety is directed against a target molecule. As will be appreciated by those in the art, the nanoparticles of the invention are can be applied locally or systemically administered (e.g., injected intravenously); thus, preferred targeting moieties are those that allow concentration of the biologically active agents in a particular localization. Thus, for example, antibodies, cell surface receptor ligands and hormones, lipids, sugars and dextrans, alcohols, bile acids, fatty acids, amino acids, peptides and nucleic acids may all be attached to localize or target the nanoparticles to a particular site.

In preferred embodiments, the targeting moiety allows targeting of the nanoparticles of the invention to a particular tissue or the surface of a cell. That is, in some embodiments, the nanoparticles of the invention need not be taken up into the cytoplasm of a cell to be activated.

In some embodiments, the targeting moiety is a peptide. For example, chemotactic peptides have been used target tissue injury and inflammation, particularly by bacterial infection; see WO 97/14443, which is incorporated herein by reference in its entirety.

In some embodiments, the targeting moiety is an antibody. The term "antibody" includes antibody fragments, as are known in the art, including Fab or $Fab_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147(1):86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology*, 14:826 (1996); Lonberg and Huszar, *Intern. Rev. Immunol.* 13:65-93 (1995).

Bispecific antibodies are monoclonal, preferably human or humanized, antibodies that have binding specificities for at least two different antigens. In the present case, one of the binding specificities is for a first target molecule and the other one is for a second target molecule.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism (see, for example, Suresh et al., *Methods in Enzymology* 121:210 (1986)).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells, including, but not limited to, HER2, VEGF, etc.

In addition, antibodies against physiologically relevant carbohydrates may be used, including, but not limited to, antibodies against markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In one embodiment, antibodies against virus or bacteria can be used as targeting moieties. As will be appreciated by those in the art, antibodies to any number of viruses (including orthomyxoviruses, (e.g., influenza virus), paramyxoviruses (e.g., respiratory syncytial virus, mumps virus, measles virus), adenoviruses, rhinoviruses, coronaviruses, reoviruses, togaviruses (e.g., rubella virus), parvoviruses, poxviruses (e.g., variola virus, vaccinia virus), enteroviruses (e.g., poliovirus, coxsackievirus), hepatitis viruses (including A, B and C), herpesviruses (e.g., Herpes simplex virus, varicella-zoster virus, cytomegalovirus, Epstein-Barr virus), rotaviruses, Norwalk viruses, hantavirus, arenavirus, rhabdovirus (e.g., rabies virus), retroviruses (including HIV, HTLV-I and -II), papovaviruses (e.g., papillomavirus), polyomaviruses, and picornaviruses, and the like), and bacteria (including a wide variety of pathogenic and non-pathogenic prokaryotes of interest including *Bacillus; Vibrio*, e.g., *V. cholerae; Escherichia*, e.g., Enterotoxigenic *E. coli, Shigella*, e.g., *S. dysenteriae; Salmonella*, e.g., *S. typhi; Mycobacterium* e.g., *M. tuberculosis, M. leprae; Clostridium*, e.g., *C. botulinum, C. tetani, C. difficile, C. peffringens; Cornyebacterium*, e.g., *C. diphtheriae; Streptococcus, S. pyogenes, S. pneumoniae; Staphylococcus*, e.g., *S. aureus; Haemophilus*, e.g., *H. influenzae; Neisseria*, e.g., *N. meningitidis, N. gonorrhoeae; Yersinia*, e.g., *G. lamblia Y. pestis, Pseudomonas*, e.g., *P.* aeruginosa, P. putida; Chlamydia, e.g., C. trachomatis; Bordetella, e.g., B. pertussis; Treponema, e.g., T. palladium; and the like) may be used.

In a preferred embodiment, the targeting moiety is all or a portion (e.g., a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-.alpha. and TGF-.beta.), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, corticotropin, follicle-stimulating hormone, glucagon, leuteinizing hormone, lipotropin, melanocyte-stimulating hormone, norepinephrine, parathyroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In another embodiment, the targeting moiety is a carbohydrate. As used herein, the term "carbohydrate" includes compounds with the general formula $Cx(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates.

In another embodiment, the targeting moiety is a lipid. As used herein, the term "lipid" includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moiety may be used to either allow the internalization of the nanoparticle to the cell cytoplasm or localize it to a particular cellular compartment, such as the nucleus. In another embodiment, the targeting moiety is all or a portion of the HIV-1 Tat protein, and analogs and related proteins, which allows very high uptake into target cells (See for example, Fawell et al., *PNAS USA* 91:664 (1994); Frankel et al., *Cell* 55:1189 (1988); Savion et al., *J. Biol. Chem.* 256:1149 (1981); Derossi et al., *J. Biol. Chem.* 269:10444 (1994); and Baldin et al., *EMBO J.* 9:1511 (1990), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLSs such as that of the SV40 (monkey virus) large T Antigen (Pro Lys Lys Lys Arg Lys Val), Kalderon (1984), et al., *Cell*, 39:499-509; the human retinoic acid receptor-β nuclear localization signal (ARRRRP); NFκB p50 (EEVQRKRQKL; Ghosh et al., *Cell* 62:1019 (1990); NFκ B p65 (EEKRKRTYE; Nolan et al., *Cell* 64:961 (1991); and others (see for example Boulikas, *J. Cell. Biochem.* 55(1):32-58 (1994), hereby incorporated by reference) and double basic NLSs exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp), Dingwall, et al., *Cell*, 30:449-458, 1982 and Dingwall, et al., *J. Cell Biol.*, 107:641-849; 1988). Numerous localization studies have demonstrated that NLSs incorporated in synthetic peptides or grafted onto reporter proteins not normally targeted to the cell nucleus cause these peptides and reporter proteins to be concentrated in the nucleus (see, for example, Dingwall, and Laskey, *Ann, Rev. Cell Biol.*, 2:367-390, 1986; Bonnerot, et al., *Proc. Natl. Acad. Sci. USA*, 84:6795-6799, 1987; Galileo, et al., *Proc. Natl. Acad. Sci. USA*, 87:458-462, 1990.

In another embodiment, targeting moieties for the hepatobiliary system are used (see U.S. Pat. Nos. 5,573,752 and 5,582,814, both of which are hereby incorporated by reference in their entirety).

In specific embodiments, a cell-binding agent is utilized as the targeting moiety. Selection of the appropriate cell-binding agent is a matter of choice that depends upon the particular cell population to be targeted, but in general monoclonal antibodies are preferred if an appropriate one is available.

The nanoparticles of the present invention can be used to deliver a biologically active agent that is cytotoxic to cancer cells. For example, the monoclonal antibody MY9 is a murine $IgG_1$ antibody that binds specifically to the CD33 antigen (J. D. Griffin et al. *Leukemia Res.*, 8: 521 (1984)) which can be used if the target cells express CD33, such as in the disease of acute myelogenous leukemia (AML). Similarly, the monoclonal antibody anti-B4 is a murine $IgG_1$ that binds to the CD19 antigen on B cells (Nadler et al., *J. Immunol.* 131: 244-250 (1983)) and can be used if the target cells are B cells or diseased cells that express this antigen, such as in non-Hodgkin's lymphoma or chronic lymphoblastic leukemia. Similarly, the antibody N901 is a murine monoclonal $IgG_1$ antibody that binds to CD56 found on small cell lung carcinoma cells and on cells of other tumors of neuroendocrine origin (Roy et al. *J. Nat. Cancer Inst.* 88:1136-1145 (1996)).

Antibodies that target solid tumors are also useful, such as the C242 antibody which binds to a carbohydrate antigen found on MUC1 present on pancreatic and colorectal tumors. (U.S. Pat. No. 5,552,293); antibody J591, which binds to PSMA (prostate specific membrane antigen) which is expressed on prostate cancer cells and on endothelial cells of neovasculature in tumors (U.S. Pat. No. 6,107,090, He Liu et al. Cancer Res. 57: 3629-3634 (1997); and antibodies to HER-2, which is overexpressed on certain breast tumors. Examples of anti-HER-2 antibodies are the TA1 antibody (L. A. Maier et al. *Cancer Res.* 51: 5361-5369 (1991)) and the 4D5 antibody (U.S. Pat. Nos. 6,387,371 and 6,399,063).

Additionally, GM-CSF, which binds to myeloid cells, can be used as a cell-binding agent to diseased cells from acute myelogenous leukemia. IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid, which targets the folate receptor expressed on ovarian and other cancers, is also a suitable cell-binding agent.

Cancers of the breast and testes can be successfully targeted with estrogen (or estrogen analogues) or androgen (or androgen analogues), respectively, as cell-binding agents.

Exemplified Embodiments

The invention includes, but is not limited to, the following embodiments:

Embodiment 1

A nanoparticle comprising an emulsified polymer having a biologically active agent covalently attached to the polymer backbone.

Embodiment 2

The nanoparticle of embodiment 1, wherein the polymer is polyacrylate or polyacrylamide.

Embodiment 3

The nanoparticle of embodiment 1 or 2, wherein the polymer is a co-polymer.

Embodiment 4

The nanoparticle of any one of embodiments 1-3, wherein the biologically active agent is a drug.

Embodiment 5

The nanoparticle of any one of embodiments 1-4, wherein the biologically active agent is an antibiotic.

Embodiment 6

The nanoparticle of any one of embodiments 1-5, wherein the antibiotic is an N-thiolated β-lactam antibiotic.

Embodiment 7

The nanoparticle of any one of embodiments 1-6, wherein the biologically active agent is covalently attached to the polymer backbone by an acryloyl amino acid.

Embodiment 8

The nanoparticle of any one of embodiments 1-7, wherein the particle further comprises a surfactant covalently attached to the polymer backbone.

Embodiment 9

The nanoparticle of any one of embodiments 8, wherein the nanoparticle comprises no surfactant that is not covalently attached to the polymer backbone.

Embodiment 10

The nanoparticle of any one of embodiments 1-8, wherein the particle further comprises unbound surfactant.

Embodiment 11

The nanoparticle of any one of embodiments 8-10, wherein the surfactant is selected from among sodium dodecyl sulfate (SDS), ammonium lauryl sulfate, other alkyl sulfate salts, sodium laureth sulfate (also known as sodium lauryl ether sulfate: SLES), Alkyl benzene sulfonate, alkyltrimethylammonium salts, cetylpyridinium chloride (CPC), polyethoxylated tallow amine (POEA), benzalkonium chloride (BAC), benzethonium chloride (BZT), dodecyl betaine, dodecyl dimethylamine oxide, cocamidopropyl betaine, and coco ampho glycinate, alkyl poly(ethylene oxide), and alkyl polyglucosides (octyl glucoside and decyl maltoside).

Embodiment 12

The nanoparticle of any one of embodiments 3-11, wherein the polymer comprises a monomer that is an acrylic or vinyl.

Embodiment 13

The nanoparticle of any of embodiments 3-11, wherein the polymer comprises a monomer selected from acrylonitrile, acrylic acid, maleic acid, methyl acrylate, ethyl acrylate, butyl acrylate, butyl methacrylate, 2-ethylhexyl acrylate, methoxyethyl acrylate, dimethylamino acrylate, methacrylic acid, isobutyl methacrylate, 2-ethyl hexyl methacrylate, lauryl methacrylate, stearic methacrylate, dimethyl amino methacrylate, allyl methacrylate, 2-hydroxyethyl acrylate, 2-hydroxy propyl acrylate, 2-hydroxy ethyl methacrylate, modified acrylamide, modified methacrylamide glycidyl acrylate, styrene, vinyl acetate, vinyl toluene, and synthetically modified acrylic.

Embodiment 14

A pharmaceutical composition comprising nanoparticles of any of embodiments 1-13; and pharmaceutically acceptable carrier.

Embodiment 15

The pharmaceutical composition of embodiment 11, wherein the nanoparticles further comprise a surfactant covalently attached to the polymer backbone.

Embodiment 16

A method for producing the nanoparticle of one of embodiments 1-12, comprising mixing the biologically active agent and a solution comprising monomers that has been pre-emulsified with a surfactant; adding an initiator to the solution; and allowing the monomers to polymerize.

Embodiment 17

A method for producing a nanoparticle, comprising co-polymerizing a monomer, a biologically active agent, and a surfactant.

DEFINITIONS

The following definitions are used, unless otherwise described.

As used herein, the term "nanoparticle" refers to a particle being less than 100 nanometers in at least one dimension (e.g., less than 100 nm in diameter).

As used herein, the term "drug" is interchangeable with the term "biologically active agent" and refers to any agent capable of having a physiologic effect (e.g., a therapeutic or prophylactic effect) on a biosystem such as prokaryotic or eukaryotic cells or organisms, in vivo or in vitro, including, but without limitation, chemotherapeutics, toxins, radiotherapeutics, radiosensitizing agents, gene therapy vectors, antisense nucleic acid constructs, transcription factor decoys, imaging agents, diagnostic agents, agents known to interact with an intracellular protein, polypeptides, and polynucleotides. Drugs that may be utilized in the nanoparticles include any type of compound including antibacterial, antiviral, anti-fungal, or anti-cancer agents that can be modified to attach a polymerizable monomer moiety. Preferably, the polymerizable moiety is an acrylic. The drug is preferably a water-insoluble or water-soluble solid or a highly viscous liquid.

The drug can be selected from a variety of known classes of drugs, including, for example, analgesics, anesthetics, anti-inflammatory agents, anthelmintics, anti-arrhythmic agents, antiasthma agents, antibiotics (including penicillins), anti-cancer agents (including Taxol), anticoagulants, antidepressants, antidiabetic agents, antiepileptics, antihistamines, antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radiopharmaceuticals, hormones, sex hormones (including steroids), time release binders, anti-allergic agents, stimulants and anoretics, steroids, sympathomimetics, thyroid agents, vaccines, vasodilators, and xanthines.

The biologically active agent need not be a therapeutic agent. For example, the beneficial effect on the subject. Further, the biologically active agent may be a diagnostic agent with no direct therapeutic activity per se, such as a contrast agent for bioimaging.

A description of these classes of drugs and diagnostic agents and a listing of species within each class can be found, for instance, in Martindale, The Extra Pharmacopoeia, Twenty-ninth Edition (The Pharmaceutical Press, London, 1989), which is incorporated herein by reference in its entirety. The drugs or diagnostic agents are commercially available and/or can be prepared by techniques known in the art.

Poorly water soluble drugs which may be suitably used in the practice of the subject invention include but are not limited to alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyridamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenyloin, piroxicam, quinapril, ramipril, risperidone, sertraline, simvastatin, sulindac, terbinafine, terfenadine, triamcinolone, valproic acid, zolpidem, or pharmaceutically acceptable salts of any of the above-mentioned drugs.

The terms "biosystem", "host", "host biosystem", "patient", "recipient", and "subject", are used interchangeably and, for the purposes of the present invention, include both prokaryotic and eukaryotic cells, such as human cells and non-human animal cells (e.g., mammal cells). Nanoparticles of the subject invention may be administered to such cells in vitro or in vivo. Thus, the methods of administration are applicable to both human therapy and veterinary applications, as well as research applications in vitro or within animal models.

As used herein, an "effective amount" of nanoparticles or of biologically active agent is that amount effective to bring about the physiological changed desired in the biosystem to which the nanoparticles are administered. The term "therapeutically effective amount" as used herein, means that amount of nanoparticles or of biologically active agent, alone or in combination with another agent according to the particular aspect of the invention, that elicits the biological or medicinal response in a biosystem that is being sought by a researcher, veterinarian, medical doctor or other clinician, which includes alleviation of the symptoms of the disease or disorder being treated.

For example, if the biologically active agent is a therapeutic agent, an effective amount of the nanoparticles of biologically active agent can be that amount sufficient to treat a pathological condition (e.g., a disease or other disorder) in the biosystem to which the nanoparticles are administered. For example, in the case of cancer, the therapeutically effective amount of the biologically active agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the agent may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "linked", "joined", "grafted", "tethered", "associated", and "conjugated" in the context of the nanoparticles of the invention, are used interchangeably to refer to any method known in the art for functionally connecting moieties (such as biologically active agents, surfactants, or targeting moieties), including, without limitation, recombinant fusion, covalent bonding, disulfide bonding, ionic bonding, hydrogen bonding, and electrostatic bonding.

The term "modified" refers to an alteration from an entity's normally occurring state. An entity can be modified by removing discrete chemical units or by adding discrete chemical units.

The term "polypeptides" refers to any polymer comprising any number of amino acids, and is interchangeable with "protein", "gene product", and "peptide".

As used in this specification, including the appended claims, the singular "a", "an", and "the" include plural reference unless the contact dictates otherwise. Thus, for example, a reference to "a nanoparticle" includes more than one such nanoparticle. A reference to "a biologically active agent" includes more than one such agent. A reference to "a cell" includes more than one such cell. A reference to "a targeting agent" includes more than one such targeting agent.

The terms "comprising", "consisting of" and "consisting essentially of" are defined according to their standard meaning. The terms may be substituted for one another throughout the instant application in order to attach the specific meaning associated with each term.

U.S. Patent Application Publication No. US2007/019160A1 (Turos et al.) and PCT Publication No. WO 2005/020933 (Turos et al.) are incorporated herein by reference in their entirety. The microemulsion polymerization method, as well as suitable surfactants, monomers, functionalities, initiators, biologically active agents (termed "bio-affecting agents") etc., are described therein.

The methods of the invention can utilize general techniques known in the field of polymer chemistry. General polymer chemistry concepts and methods that may be utilized are described in the Polymer Handbook (4$^{th}$ Edition), eds., Brandup et al., New York, John Wiley and Sons, 1999; and Polymer Synthesis and Characterization: A Laboratory Manual, eds. Sandler et al., Academic Press, 1998. The practice of the subject invention can employ, unless otherwise indicated, conventional techniques of molecular biology, microbiology, recombinant DNA technology, electrophysiology, and pharmacology, which are within the ordinary skill in the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

Following are examples that illustrate procedures for practicing the invention. These examples should not be construed as limiting. All percentages are by weight and all solvent mixture proportions are by volume unless otherwise noted.

EXAMPLE 1

Polyacrylate Emulsion in Antibacterial Application

Synthesis and characterization of emulsified polyacrylate nanoparticle antibacterials for drug delivery of water-insoluble antibiotics is described. These nanoparticles can be prepared in aqueous media directly from acrylate monomers through free radical microemulsion polymerization. These emulsions contain antibiotic-conjugated polyacrylate nanospheres measuring 30-40 nm in diameter and have antibacterial activity against drug-resistant forms of Staphylococcus aureus (MRSA).

Figure 8:
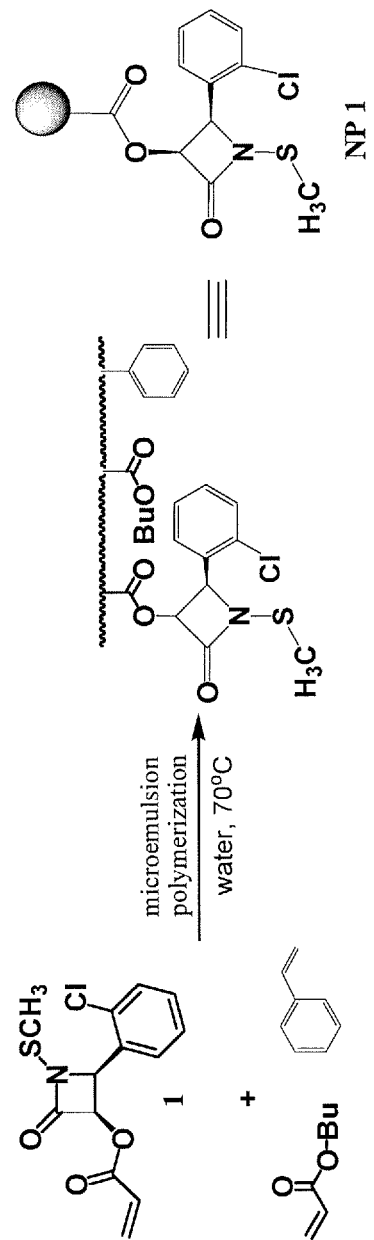
FIG. 8 shows a scheme for synthesizing an antibiotic-conjugated nanoparticle (NP1) using emulsion polymerization.
Figure 9A:
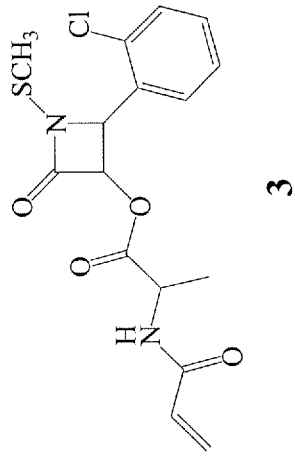
FIGS. 9A-9D show four N-acryloyl amino acid-linked β-lactam antibiotics (2, 3, 4, and 5, respectively). These lactam acrylates (2-5) were used to produce nanoparticles NP2, NP3, NP4, and NP5, respectively.
Figure 9B:
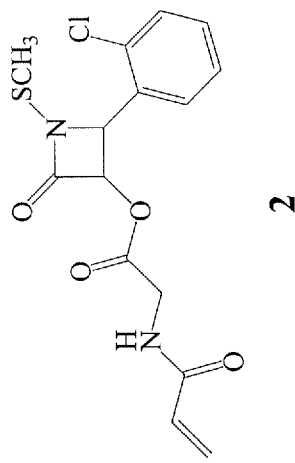
Figure 9C:
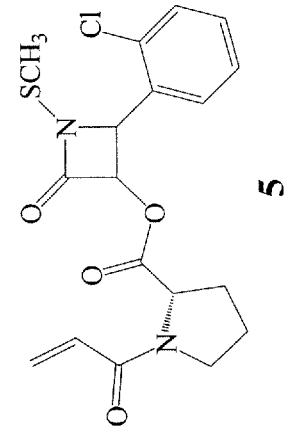
Figure 9D:
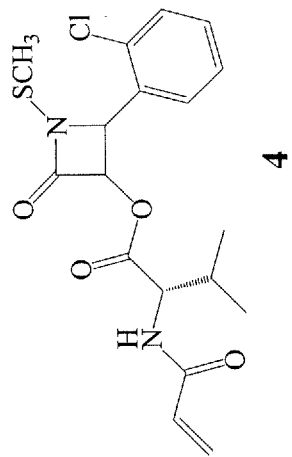

Antibiotic-conjugated nanoparticles, in which the drug is covalently attached to the polymer backbone making up the nanoparticle were prepared by emulsion polymerization. The general procedure involves dissolving a water-insoluble drug as its acrylate derivative in a liquid acrylate. The mixture of acrylate monomers are first pre-emulsified in aqueous media by addition of 3% of surfactant to create a homogenous solution. Upon subjection of an initiator, the acrylate monomers undergo free radical polymerization at 70° C. to produce a milky white emulsion. Formulation and reaction conditions of polymerization are shown in Table 1. The reaction scheme is shown in FIG. 8.

TABLE 1

Formulation and Reaction Conditions

| Component | Amount |
|---|---|
| Beta-lactam | 10 mg |
| Butyl acrylate | 700 mg |
| Styrene | 300 mg |
| Surfactant | 30 mg |
| Radical Initiator | 10 mg |
| Water | 4 ml |
| Reaction Temperature | 70° C. |

A. Physical Properties of Nanoparticle Polymers

Figure 4A:
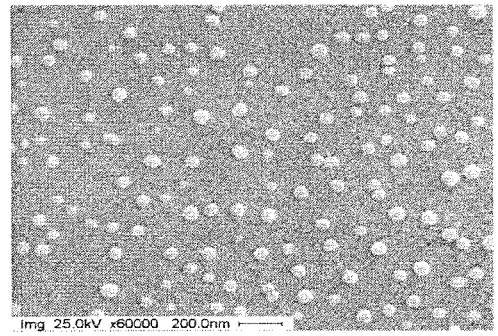
FIGS. 4A and 4B show a scanning electron micrograph and a transmission electron micrograph, respectively, showing "surfactant-free" nanoparticles of the invention, i.e., having surfactant covalently attached to the polymer backbone (prepared as shown in FIG. 3).
Figure 4B:
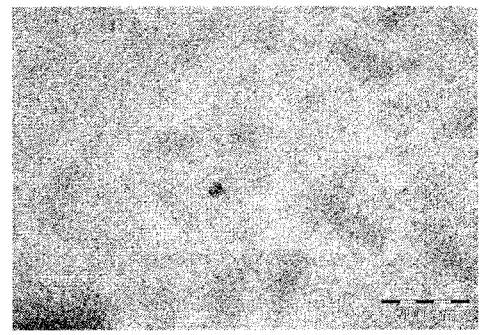

Analysis of the nanoparticle polymers by scanning electron microscopy (SEM), transmission electron microscopy (TEM), and dynamic light scattering (DLS) indicate the particles have spherical shape with average diameters of 35 nm. Zeta potential analysis of these emulsified nanoparticles showed the surface charge at neutral pH to be approximately −61 mV. Results of SEM and TEM are shown in FIGS. 4A and 4B, respectively.

B. Effect of Changing the Functionality of the Drug Monomer

In this experiment, four N-acryloyl amino acid-linked β-lactam antibiotics (2-5, FIGS. 9A-9D, respectively) were prepared from the reaction between N-acryloyl amino acids and $C_3$-hydroxy methylthio β-lactam, and used for the polymerization under the described conditions to see if the polymerized nanoparticles have different levels of effectiveness against MRSA. These nanoparticles are labeled as NM, NP2, NP3, NP4, and NP5 based on the structures of the lactam acrylates 1-5 (shown in FIGS. 8 and 9A-9D, respectively).

Figure 10:
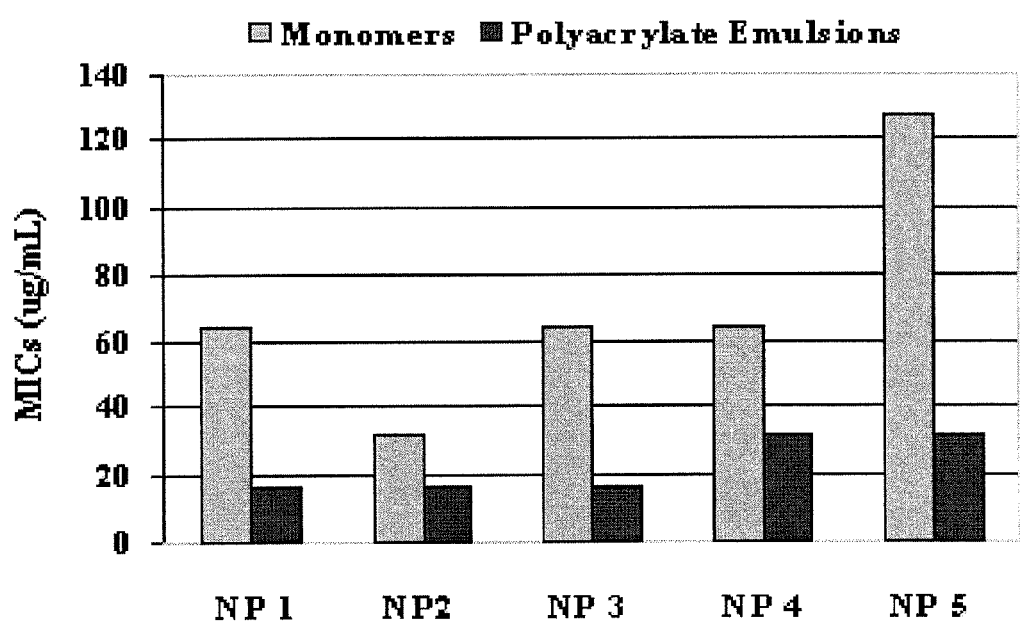
FIG. 10 is a graph showing the minimum inhibitory concentrations (MICs) in micrograms per milliliter of nanoparticles NP1, NP2, NP3, NP4, and NP5 against 9 clinical strains of drug resistant *Staphylococcus aureus* (MRSA) by the Kirby-Bauer method.

C. Comparison of Antibacterial Activities of the Emulsified Polymers and Monomers Against MRSA These polyacrylate nanoparticles were evaluated for antibacterial activities against 9 clinical strains of MRSA by Kirby-Bauer well diffusion on agar plates and minimum inhibitory concentration (MICs) determinations in broth. Bars in the graph of FIG. 10 indicate the average MICs (μg/mL) of the drug monomers and the nanoparticles, respectively. Nanoparticles NP1-3 showed enhanced growth inhibition against MRSA with MICs of approximately 16 μg/mL. Branching within the side chain of amino acids (as demonstrated by nanoparticle NP4) and having a ring in the acrylate tether (as demonstrated by NP5) slightly increase the nanoparticle activities against MRSA. MICs measured for nanoparticles NP4-5 in broth media were approximately 32 μg/mL.

D. Nanoparticle-Based Delivery of an Antibiotic into Staphylococcus aureus

Figures 1, 2, 11:
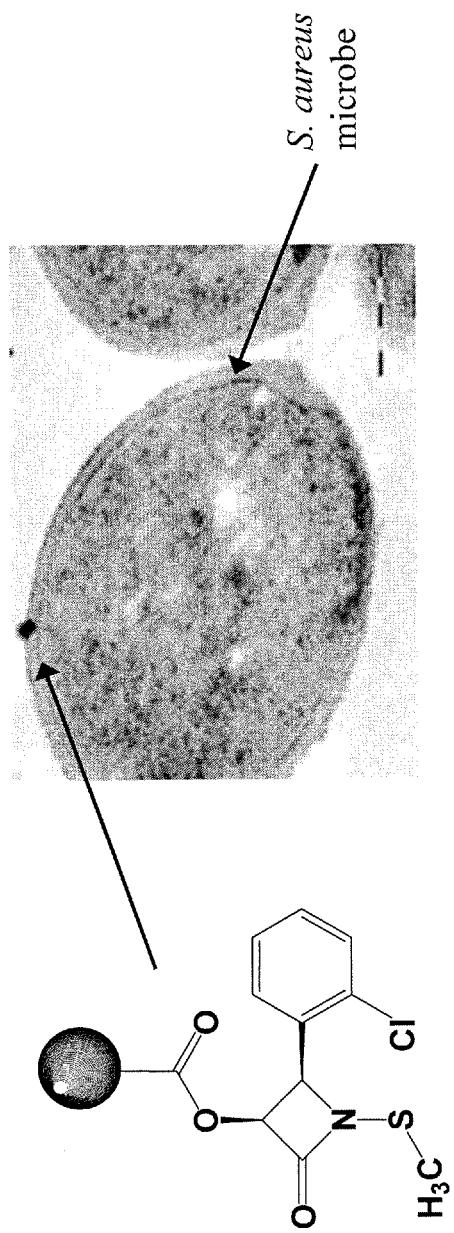

The drug delivery system in this experiment is based on synthesis of polyacrylate nanoparticles which contain covalently attached N-thiolated β-lactam antibiotics (for controlled drug release). Without being bound by theory, the inventors propose that the polyacrylate acts as a prodrug, with enzymatic release of the drug into the microbe upon interaction with its membrane (see FIGS. 11-1 and 11-2).

EXAMPLE 2

Surfactant Plus Control Nanoparticles

The control nanoparticles were added to the wells as an emulsion having 5% solid content, which reduced the amount of surfactant to 0.75%; therefore, more surfactant was added to the emulsion prior to placement in the cell-containing wells in order to reach the designated amounts of surfactant being tested. When combined with control nanoparticles prior to addition to healthy fibroblasts, the surfactant was much less toxic than when added to the cells without the control nanoparticles. This may be due to interactions of the surfactant with the nanoparticles, which may prohibit the surfactant from interacting with the cells. The results show that 1% surfactant is the least toxic and that 9% surfactant kills all of the cells present in the well. FIG. 1 shows the effect of dodecyl sulfate combined with control nanoparticles against human dermal fibroblasts.

EXAMPLE 3

Synthesis of Polymerizable Surfactants and the Influence of Charge

Figure 2:
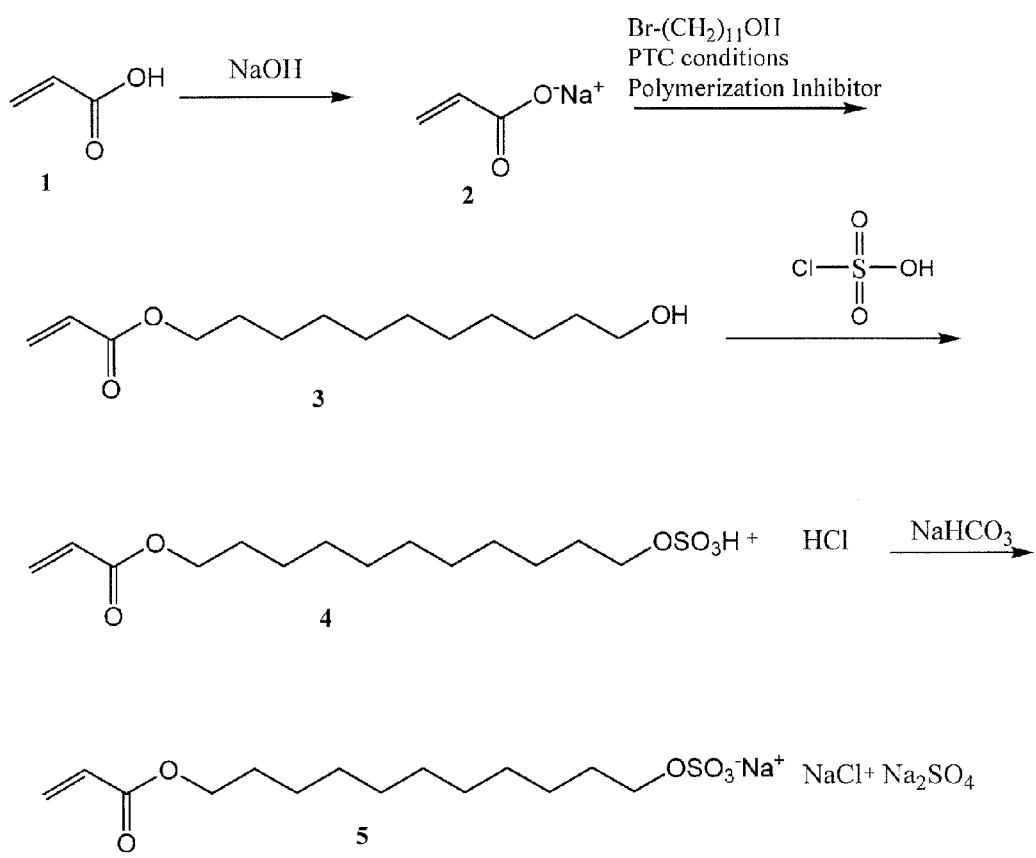
FIG. 2 shows a scheme for synthesizing sodium 11-acryloloxy undecan-1-yl sulfate.

Synthesis and screening of polymerizable surfactants with anionic, cationic, neutral and zwitterionic character were carried out to evaluate the influence of the charge on the effectiveness of the drug delivery system. FIG. 2 shows the schematic pathway utilized to synthesize sodium 11-acryloloxy undecan-1-yl sulfate.

A. Synthesis of Methacrylate Salt, 2.

Method (Unzue, M. et al., *J. Appl. Polym. Sci.*, 1997, 66:1803): Sodium hydroxide (276.6 g, 0.69 mol) dissolve un-deionized water was placed in a round-bottom flask and kept in a bath for 10 minutes. Acrylic acid (59.75 g., 0.69 mol) was added drop wise under stirring to the above solution. After 30 minutes, the reaction mixture was freeze-dried. The product was dissolved in methanol and precipitated with diethyl ether. After filtering, a white powder (71.14 g, 0.65 mol) was obtained in 95% yield.

B. Synthesis of 11-acryloloxy undecan-1-01, 3.

Method (Unzue, M. et al., *J. Appl. Polym. Sci.*, 1997, 66:1803): Sodium acrylate (70 g, 0.65 mol), 11-bromoundecan-1-ol (36.95 g, 0.148 mol0, N-tetrabutylammonium bromide (13.86 g, 0.04 mol), 2,6,-di-t-butyl-4-methyl phenol (75 mg, 0.34 mmol) dissolved in deionized water (130 ml) and chlorofoiin (70 ml), were placed in a round-bottom flask. The reaction vessel was placed in an oil bath at 100° C., and vigorous magnetic stirring was applied for three days. After that time, the chloroform layer was washed with 2% sodium hydroxide solution (4×250 ml) and distilled water (4×250 ml). Organic layer was dried over magnesium sulfate, and the solvent evaporated. A yellowish viscous liquid (29.42 g, 0.11 mol) was obtained. The latter was distilled in a Kugelrohr under vacuum (0.01 mm Hg) at 190° C., yielding a viscous clear liquid (23.63 g, 0.09 mol) in 62% yield.

C. Synthesis of Sodium 11-Acryloloxy undecan-1-yl Sulfate, 5.

Method (Unzue, M. et al., *J. Appl. Polym. Sci.*, 1997, 66:1803): Chlorosulfonic acid (8.65 g, 0.074 mol) was placed in a three-necked round bottom flask, which was fitted with mechanical stirrer, a dropping funnel, and a nitrogen inlet. 11-acryloyloxy undecan-1-ol, compound 3, (19 g, 0.074 mol) was added dropwise over one hour with vigorous stirring. The reaction mixture was then stirred for two hours and purged with nitrogen for two hours more. The mixture at this point was brown viscous liquid, which was added dropwise to a saturated sodium hydrogen carbonate ice solution (20 ml) with vigorous stirring. During the addition process, the mixture was kept basic by adding the sodium hydrogen carbonate, as required. Isopropanol (56 ml) and water (90 ml) were then filtered off, and the filtrate washed with petroleum ether of 40-60° C. (2×40 ml). The sample was freeze-dried, yielding a light yellow solid (35 g), in 130% yield. This means that a relatively low purity surfmer was obtained.

D. Results

Since the purification process of the nanoparticles is a main issue to make sure that biological activity comes exclusively from the drug attached to the nanoparticle, the methods utilized for the purification and characterization of the nanoparticle emulsions are important. Table 2 summarizes some preliminary results of the effect of centrifugation and dialysis on the physical properties of nanoparticles.

TABLE 2

Effect of the centrifugation and dialysis in the zeta potential and size of the nanoparticle in emulsion prepared with different concentrations of the acrylated sulfate surfactant monomer.

| Concentration of Biotin monomer in the polymeric emulsion | Zeta Potential (mV) | | | Size of the Particle (nm) | | |
|---|---|---|---|---|---|---|
| | Initial | Dialyzed | Centrifug. | Initial | Dialyzed | Centrifug. |
| 3% | −69.8 | −31.6 | −28.9 | 47 | 46 | 34 |
| 11% | −77.9 | −29.3 | −31.7 | 35 | 27 | 26 |
| 20% | −40.0 | −27.1 | −22.4 | 71 | 68 | 72 |

EXAMPLE 4

Surfactant-Free Nanoparticles for Delivery of Antibiotics and Other Biologically Active Agents One of the disadvantages encountered with polymeric antibiotics is that the surfactant used for the polymerization can leach away from the nanoparticle in sufficient concentrations to cause cytotoxicity in human fibroblasts. To avoid this, nanoparticles in which the surfactant moiety is covalently attached to the backbone of the polymer can be utilized.

A. Preparation of Nanoparticles

Figure 3:
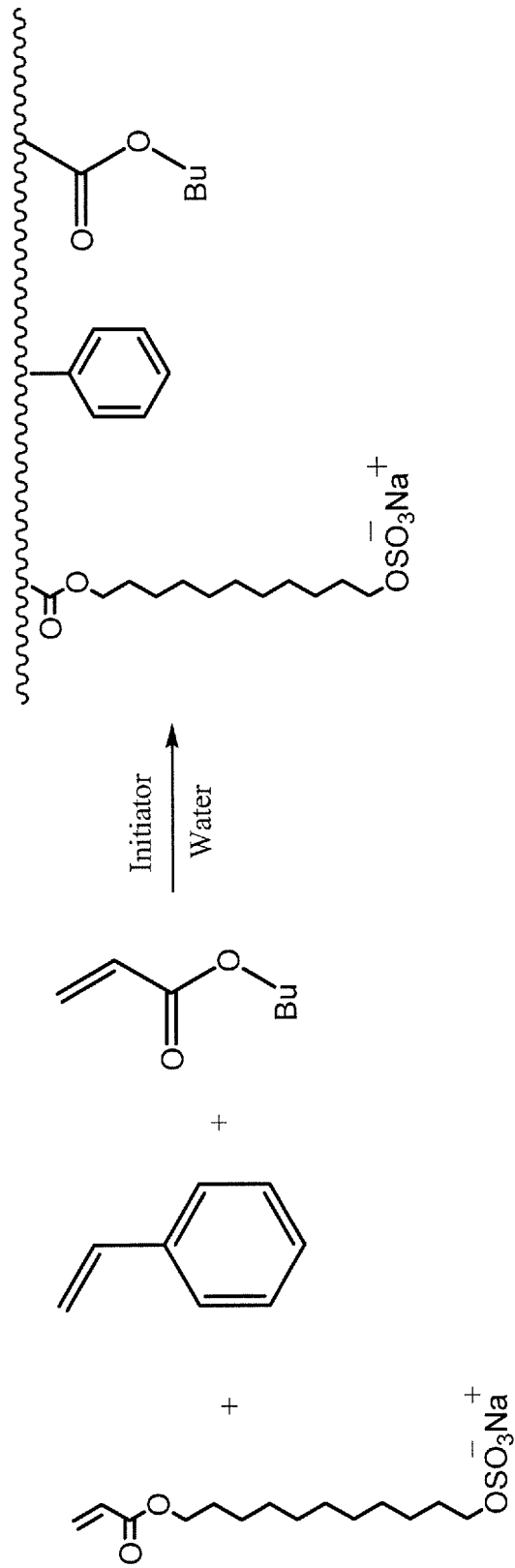
FIG. 3 shows a scheme for synthesizing an embodiment of nanoparticles of the invention.
Figure 5:
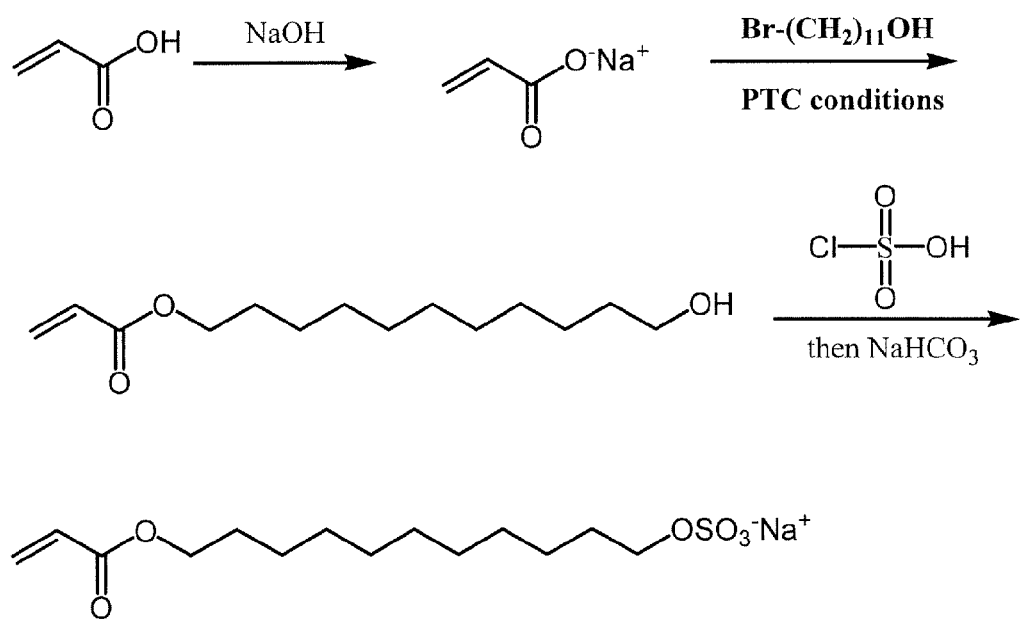
FIG. 5 shows a scheme for synthesizing "surfactant-free" acrylate monomers in accordance with an embodiment of the invention.
Figure 6A:
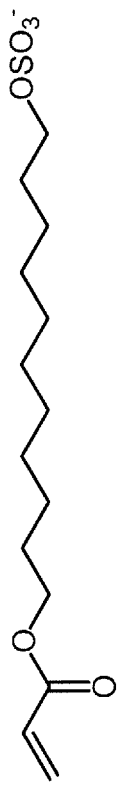
FIGS. 6A-6D show, respectively, anionic, cationic, neutral, and Zwitterionic surfactants.
Figure 6B:
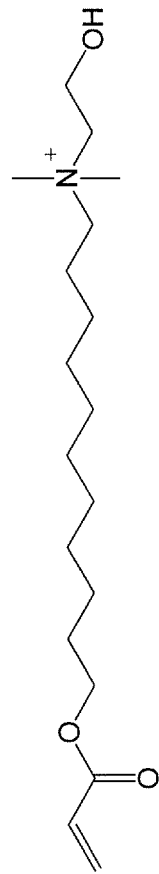
Figure 6C:
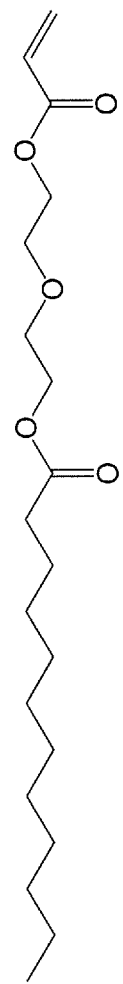
Figure 6D:
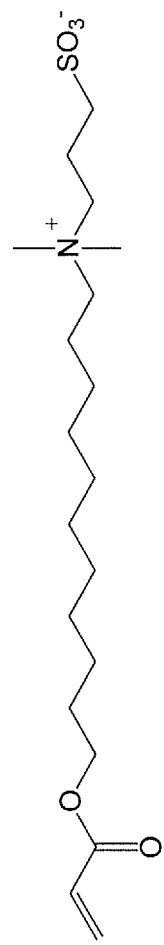

FIG. 3 shows a scheme for synthesizing an embodiment of nanoparticles of the invention. FIG. 5 shows a scheme for the synthesis of "surfactant-free" acrylate monomers. FIGS. 6A-6D show the chemical structures of synthesized polymerizable surfactants (anionic, cationic, neutral, and Zwitterionic, respectively). Formulation and conditions of microemulsion polymerization are shown in Table 3.

TABLE 3

Formulation and Conditions of Microemulsion Polymerization

| Components | Antibiotic monomer | Butyl acrylate | Styrene | Surfactant/ Surfmer | Radical Initiator | Water |
|---|---|---|---|---|---|---|
| Amounts | 3% | 27% | 70% | 3% | 1% | 4 mL |

B. Purification of Nanoparticles

Nanoparticles were purified by centrifugation and dialysis. To centrifuge, 1 mL sample per 2 mL vial was centrifuged at 12K-13K rpm (16.1K×g) for 30 minutes. Dialysis was performed with membrane tubing with 6K-8K mMWCO for 24 hours.

C. Characterization of Nanoparticles

The following operations were conducted (and results observed): proton nuclear magnetic resonance imaging (NMR); scanning and transmission electron microscopy; zeta potential analysis (−42 mV at neutral pH); dynamic light scattering analysis (average diameter of particle is 40 nm); and stability testing at different temperature and pH solutions.

As shown in Table 4, tandem dialysis-centrifugation removes both charged and larger open chain impurities without damaging the nanoparticles (size is unaffected, as measured by dynamic light scattering (DLS).

TABLE 4

Effects of dialysis-centrifugation on charge and particle size.

| Concentration of monomer in Polymer | Zeta Potential (mV) | | | Size of the particle (nm) | | |
|---|---|---|---|---|---|---|
| | Initial | Dialysis | Centf. | Initial | Dialysis | Centf. |
| 3% | −69.8 | −31.6 | −28.9 | 47 | 46 | 34 |
| 11% | −77.9 | −29.3 | −31.7 | 35 | 27 | 26 |
| 20% | −40.0 | −27.1 | −22.4 | 71 | 68 | 72 |

FIGS. 4A and 4B show a scanning electron micrograph and a transmission electron micrograph, respectively, showing "surfactant-free" nanoparticles of the invention, i.e., having surfactant covalently attached to the polymer backbone (prepared as shown in FIG. 3).

Figure 7A:
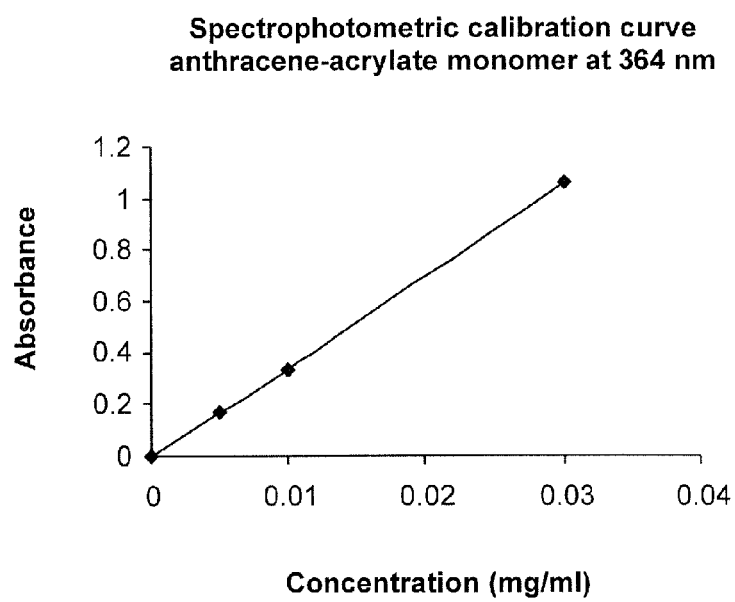
FIGS. 7A and 7B show the results of ultra-violet spectrophotometric studies on anthracene-acrylate nanoparticles produced using the method of the invention.
Figure 7B:
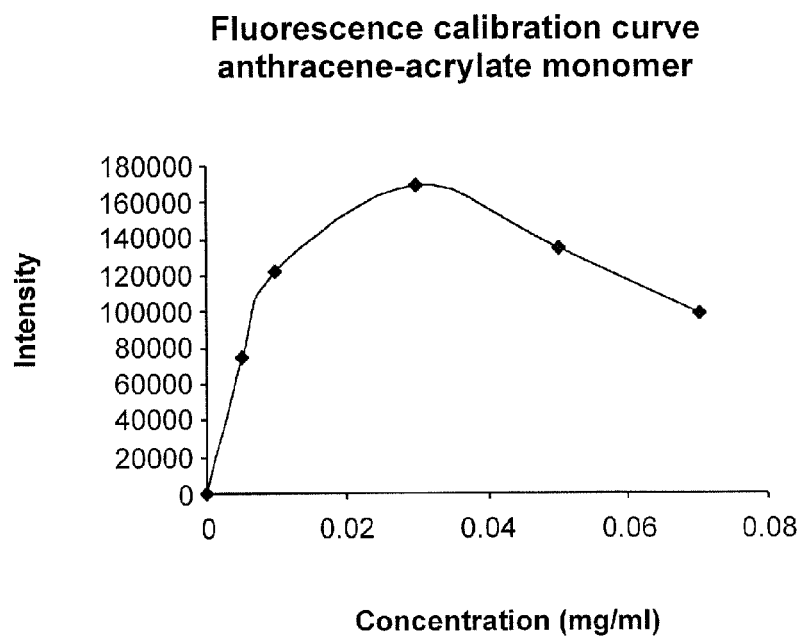

D. Ultraviolet-Spectrophotometric Studies on Anthracene-Acrylate Nanoparticles Acrylated anthracene monomer was used to monitor the concentration of nanoparticles during the purification process by UV-spectrophotometric and fluorescent studies. FIG. 7A is a graph showing a spectrophotometric calibration curve for anthracene-acrylate monomer at 364 nanometers. FIG. 7B is a graph showing a fluorescence calibration curve for anthracene-acrylate monomer.

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A nanoparticle comprising an emulsified polymer, a surfactant, and a biologically active agent, wherein said biologically active agent and said surfactant are covalently attached to the polymer backbone of said polymer, and wherein the nanoparticle comprises no surfactant that is not covalently attached to the polymer backbone.

2. The nanoparticle of claim 1, wherein the polymer is polyacrylate or polyacrylamide.

3. The nanoparticle of claim 1, wherein the polymer is a co-polymer.

4. The nanoparticle of claim 1, wherein the biologically active agent is a water-insoluble drug.

5. The nanoparticle of claim 1, wherein the biologically active agent is an antibiotic.

6. The nanoparticle of claim 5, wherein the antibiotic is an N-thiolated β-lactam antibiotic.

7. The nanoparticle of claim 1, wherein the biologically active agent is covalently attached to the polymer backbone by an acryloyl amino acid.

8. A pharmaceutical composition comprising nanoparticles and a pharmaceutically acceptable carrier, wherein said nanoparticles comprise an emulsified polymer, a surfactant, and a biologically active agent, wherein said biologically active agent and said surfactant are covalently attached to the polymer backbone of said polymer and wherein said nano articles comprise no surfactant that is not covalently attached to the polymer backbone.

9. A method for producing a nanoparticle, comprising mixing a biologically active agent and a solution comprising monomers that have been pre-emulsified with a polymerizable surfactant; adding an initiator to the solution; and allowing the monomers to polymerize, wherein the resulting nanoparticle comprises an emulsified polymer, the surfactant, and the biologically active agent, wherein the biologically active agent and the surfactant are covalently attached to the polymer backbone of the polymer, and wherein the nanoparticle comprises no surfactant that is not covalently attached to the polymer backbone.

10. A method for producing a nanoparticle, comprising co-polymerizing a monomer, a biologically active agent, and a polymerizable surfactant wherein the biologically active agent and the surfactant are covalently attached to the polymer backbone of the resulting polymer, and wherein the nanoparticle comprises no surfactant that is not covalently attached to the polymer backbone.

11. The nanoparticle of claim 1, wherein said surfactant is an acrylated surfactant.

12. The pharmaceutical composition of claim 8, wherein said surfactant is an acrylated surfactant.

13. The method of claim 9, wherein the polymerizable surfactant is an acrylated surfactant.

14. The method of claim 10, wherein the polymerizable surfactant is an acrylated surfactant.

15. The pharmaceutical composition of claim 8, wherein said biologically active agent is an antibiotic.

16. The method of claim 9, wherein the biologically active agent is an antibiotic.

17. The method of claim 10, wherein the biologically active agent is an antibiotic.

* * * * *

UNITED STATES PATENT AND TRADEMARK OFFICE
CERTIFICATE OF CORRECTION

PATENT NO. : 8,414,926 B1
APPLICATION NO. : 11/854380
DATED : April 9, 2013
INVENTOR(S) : Edward Turos et al.

It is certified that error appears in the above-identified patent and that said Letters Patent is hereby corrected as shown below:

In the Specifications:

Column 1,
Lines 16-20, "The subject matter of this application has been supported by research grants from the National Institutes of Health under grant number RO1 AI51351 and the National Science Foundation under grant number DGE 0221681. Accordingly, the government has certain rights in this invention."

should read

--This invention was made with government support under Grant #AI051351 awarded by the National Institutes of Health and Grant #DGE0221681 awarded by the National Science Foundation. The government has certain rights in the invention.--.

Column 4,
Line 2, "respectively." should read --respectively).--.

Column 6,
Line 37, "invention are can be" should read --invention can be--.
Line 52, "used target" should read --used to target--.

Column 13,
Line 46, "For example, the beneficial effect on the subject."

should read

--For example, the agent may be cytotoxic to the local cells to which it is delivered but have an overall beneficial effect on the subject.--.

Column 16,
Line 34, "3-lactam" should read --β-lactam--.
Line 39, "NM" should read --NP1--.

Column 17,
Line 61, "0.148 mol0" should read --0.148 mol)--.
Line 64, "chlorofoiin" should read --chloroform--.

Signed and Sealed this
Thirteenth Day of August, 2013

Teresa Stanek Rea
*Acting Director of the United States Patent and Trademark Office*

CERTIFICATE OF CORRECTION (continued)
U.S. Pat. No. 8,414,926 B1

Column 19,
Line 26, "(DLS)." should read --(DLS)).--.
Lines 44-45, "Anthracene-Acrylate Nanoparticles Acrylated anthracene monomer was"

should read

--Anthracene-Acrylate Nanoparticles
           Acrylated anthracene monomer was--.

In the Claims:

Column 20,
Lines 26-27, "nano articles" should read --nanoparticles--.